(12) United States Patent
Ashoori et al.

(10) Patent No.: US 9,858,388 B1
(45) Date of Patent: Jan. 2, 2018

(54) HEALTH MONITORING USING PARALLEL COGNITIVE PROCESSING

(71) Applicant: International Business Machines Corporation, Armonk, NY (US)

(72) Inventors: Maryam Ashoori, White Plains, NY (US); Benjamin D. Briggs, Waterford, NY (US); Lawrence A. Clevenger, Rhinebeck, NY (US); Leigh Anne H. Clevenger, Rhinebeck, NY (US); Jonathan H. Connell, II, Cortlandt-Manor, NY (US); Nalini K. Ratha, Yorktown Heights, NY (US); Michael Rizzolo, Albany, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/275,672

(22) Filed: Sep. 26, 2016

(51) Int. Cl.
*G06Q 10/00* (2012.01)
*G06F 19/00* (2011.01)

(52) U.S. Cl.
CPC ........ *G06F 19/3431* (2013.01); *G06F 19/321* (2013.01); *G06F 19/3406* (2013.01); *G06F 19/3443* (2013.01)

(58) Field of Classification Search
CPC .............. G01J 2005/0081; G06K 9/00; G06T 2207/10048; G06T 2207/30201; G06T 7/0028; H04N 7/181
See application file for complete search history.

(56) References Cited

U.S. PATENT DOCUMENTS 6,996,256 B2  2/2006  Pavlidis
9,007,432 B2  4/2015  Chuang et al.
(Continued)

FOREIGN PATENT DOCUMENTS

CN    103727593 A    4/2014
CN    104697110 A    6/2015
(Continued)

OTHER PUBLICATIONS

Afghani et al. et al.; Ttl: On Stage Performer Tracking System; Publication Ttl: International Journal of Advances in Engineering & Technology, vol. 3, No. 2, pp. 65; 2012; Publisher: I A E T Publishing House; Country of Publication: USA; 12 pages.
(Continued)

*Primary Examiner* — Reginald R Reyes
(74) *Attorney, Agent, or Firm* — Cantor Colburn LLP; Yeen Tham

(57) ABSTRACT

A system for monitoring participants in a group includes one or more thermal image capturing devices configured to capture one or more thermal images of a plurality of participants in an event, and a processing device configured to receive the one or more thermal images and identification data for at least one of the plurality of participants. The processing device is configured to perform a method that includes identifying the at least one of the plurality of participants, calculating a heat profile of the at least one of the plurality of participants, comparing the heat profile to a reference profile, and determining whether a deviation exists between the heat profile and the reference profile. The method also includes, based on detecting the deviation, calculating a magnitude of the deviation and determining whether a health risk exists based on the magnitude of the deviation.

20 Claims, 6 Drawing Sheets

(56) References Cited

U.S. PATENT DOCUMENTS

| | | | |
|---|---|---|---|
| 9,317,660 B2 | 4/2016 | Burich et al. | |
| 2010/0189313 A1 | 7/2010 | Prokoski | |
| 2011/0215930 A1* | 9/2011 | Lee | G06K 9/00 340/573.1 |
| 2013/0207998 A1* | 8/2013 | Aoki | G06F 3/00 345/619 |
| 2013/0342691 A1* | 12/2013 | Lewis | H04N 5/332 348/143 |
| 2014/0204217 A1* | 7/2014 | Sohn | G01J 5/0859 348/164 |
| 2014/0243683 A1 | 8/2014 | Xiao et al. | |
| 2016/0086500 A1 | 3/2016 | Kaleal, III | |

FOREIGN PATENT DOCUMENTS

| | | |
|---|---|---|
| WO | 2015086855 A1 | 6/2015 |
| WO | 2015142877 A1 | 9/2015 |

OTHER PUBLICATIONS

Cortinas et al.; Ttl: TCNJ Athlete Tracker; Publication Ttl: 2015 41st Annual Northeast Biomedical Engineering Conference (NEBEC); 2015; Publisher: IEEE; Country of Publication: USA; 3 pages.

* cited by examiner

HEALTH MONITORING USING PARALLEL COGNITIVE PROCESSING

BACKGROUND

The present invention relates generally to monitoring groups of people, and more specifically, to monitoring groups during athletic events or other gatherings and identifying health risks to individual participants.

When amateur or professional athletes participate in sporting events, there is a risk of heatstroke or hypothermia which may go unnoticed by the athlete during their competition, but can be a health risk if not addressed by cooling off or warming up as appropriate. For example, when temperature is incrementally higher, it can significantly affect occurrence of heatstroke, particularly owing to the fact that symptoms often manifest only after a critical point is reached.

In addition, participants may not have wearable temperature sensors, due to preference or limitations on wearables for that sport. In such instances, large numbers of participants make individualized health tracking and health event prediction difficult for race organizers and medical staff.

SUMMARY

Embodiments include a method, system, and computer program product for monitoring participants in a group. In accordance with one or more embodiments, a system for monitoring participants in a group includes one or more thermal image capturing devices disposed at a location configured to capture one or more thermal images of a plurality of participants in an event, and a processing device communicably coupled to the one or more thermal image capturing devices, the processing device configured to receive the one or more thermal images and identification data for at least one of the plurality of participants. The processing device is configured to perform a method that includes identifying the at least one of the plurality of participants based on the identification data, calculating a heat profile of the at least one of the plurality of participants based on the one or more thermal images, comparing the heat profile to a reference profile, and determining whether a deviation exists between the heat profile and the reference profile. The method also includes, based on detecting the deviation, calculating a magnitude of the deviation and determining whether a health risk exists based on the magnitude of the deviation, and generating a notification based on determining that the health risk exists.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE DRAWINGS

The subject matter of the present disclosure is particularly pointed out and distinctly claimed in the claims at the conclusion of the specification. The foregoing and other features and advantages of the one or more embodiments disclosed herein are apparent from the following detailed description taken in conjunction with the accompanying drawings, in which:

DETAILED DESCRIPTION

There are provided methods, devices, systems and computer program products for monitoring and mitigation of health risks to individuals participating in a group event, such as a sporting event or social event.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Figure 1:
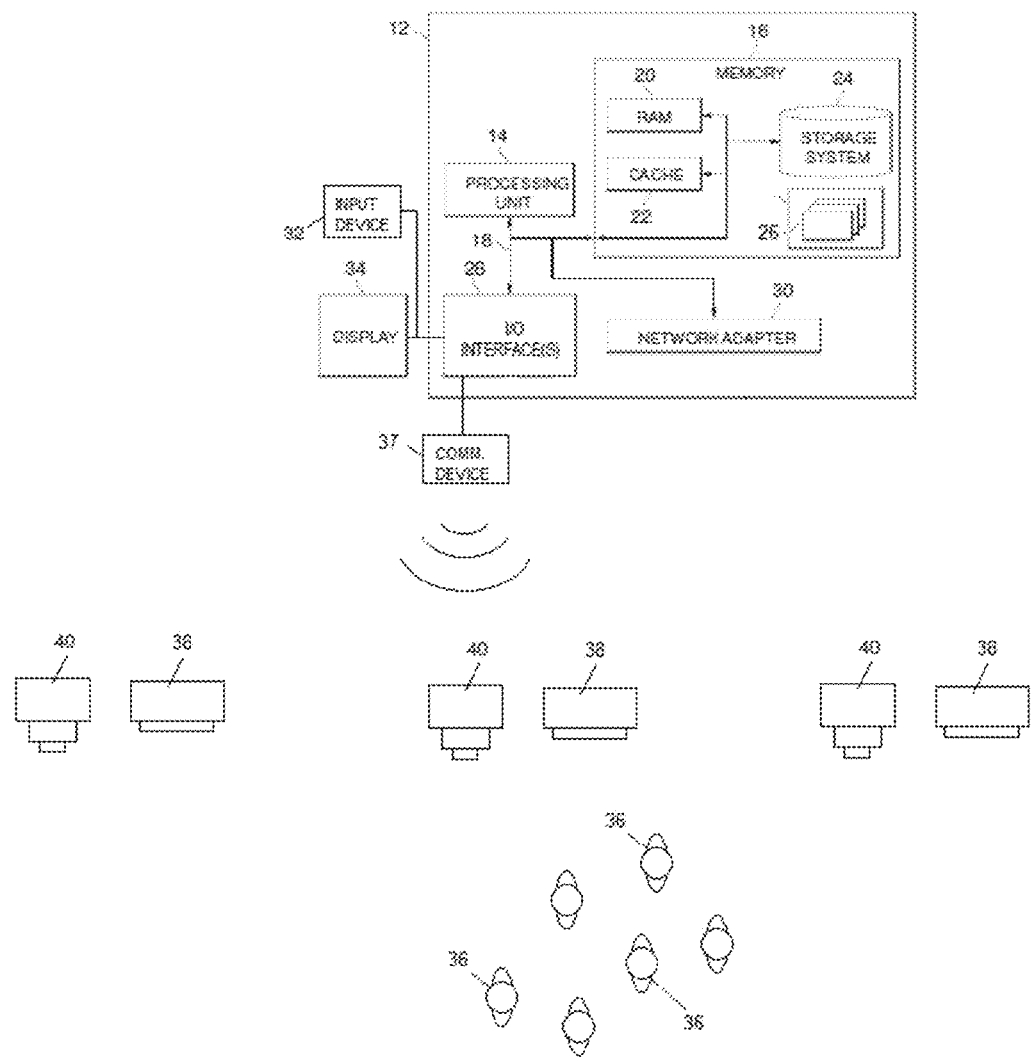
FIG. 1 depicts a computing system according to an embodiment of the present invention.

FIG. 1 depicts a computer system 11 according to an embodiment of the present invention. The computing system 11 can be used to perform various actions, including receiving and processing user inputs and performing various processing actions as described herein, including storing and processing data, executing programs and displaying information. The computing system is configured to receive requests or commands to perform health monitoring operations.

The computing system 11 includes a processing device 12, such as a computer, server, laptop or mobile device. Components of the processing device 12 may include, but are not limited to, one or more processors or processing units 14, a memory 16, and a bus 18 that couples various system components including the memory 16 to the processing unit 14. As discussed further below, the processing device 12 may be configured as part of a central controller or processor that communicates with multiple mobile machines, and/or may be incorporated in one or more of the mobile machines.

The processing device 12 typically includes a variety of computer system readable media. Such media may be any available media that is accessible by the processing device 12, and includes both volatile and non-volatile media, removable and non-removable media.

The memory 16 can include computer system readable media in the form of volatile memory, such as a random access memory (RAM) 20 and/or cache memory 22. The processing device 12 may further include other removable/non-removable, volatile/non-volatile computer system storage media. For example, a storage system 24 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 18 by one or more data media interfaces. As will be further depicted and described below, the memory 16 may include at least one program product having a set (e.g., at least one) of program modules 26 that are configured to carry out the functions of embodiments described herein.

The processing device 12 includes or is connected to various components, which may be incorporated in the device 12 or external to the device 12. The device 12 includes interfaces 28 for communication with components and may also include a network adapter 30 for communication with other devices or components over a suitable network or remote connection. The device 12 is connected to or includes at least one input device 32 such as a keyboard, button, mouse and/or touchscreen, and a display 34.

The processing device 12 can communicate with one or more networks such as a local area network (LAN), a general wide area network (WAN), and/or a public network (e.g., the Internet) via the network adapter 30. As depicted, the network adapter 20 communicates with the other components of the processing device 12 via the bus 18.

The processing device 12 may also include communication components for communicating with one or more monitoring devices for monitoring of health aspects of various participants 36 in a sporting event, social event or other gathering. The communication components may include network components such as the adapter 30, wired connections and/or wireless communication devices.

In one or more embodiments, the processing device 12 includes a wireless communication device 37 such as an antenna assembly for transmitting and receiving radio communications. Such radio communications can be performed using devices having various ranges, such as long range communication devices and short range devices such as Bluetooth and Wi-Fi.

The processing device 12 communicates with the monitoring devices to, e.g., receives data to be used in identifying and monitoring individual participants within a group. For example, the monitoring devices include one or more thermal image capturing devices configured to collect thermal images (e.g., still and/or video) of the group of parts thereof. In one or more embodiments, the one or more thermal image capturing devices include infrared (IR) cameras 38 positioned at one or more suitable locations so as to capture IR images of the group or of parts thereof. Embodiments are described herein with reference to IR cameras and images, however it should be understood that references to infrared or IR cameras and images are intended to encompass any suitable thermal image capturing devices and any suitable thermal images.

In addition, the monitoring devices may include one or more visible spectrum cameras 40 (referred to herein as cameras or visible light cameras) positioned at one or more suitable locations so as to capture visible images of the group or of parts thereof. Although embodiments are described herein in conjunction with still images, they are not so limited and can apply to video recordings taken by IR and/or visible light recording devices.

The processing device 12 may also communicate with devices worn by individual participants, such as an identification chip or tag, wearable device (e.g., smartwatch or fit bit type device) or mobile device (e.g., smartphone). It is noted that the monitoring devices are not limited to the specific examples described herein, and may be any suitable type of device that can be used to identify and/or monitor participants. In one or more embodiments, the processing device 12 and the IR cameras form aspects of a monitoring subsystem that includes a monitoring module in the processing device 12. The monitoring module is configured to receive IR images that record the temperatures of individuals in the group.

The program modules 26 are configured to perform aspects of monitoring methods described herein. For example, a fusion subsystem includes a program module 26 configured as an image processing module that receives visible images from cameras and performs facial recognition, determines identifiable features (e.g., clothing color or pattern, or a tag such as a participant number displayed on the participant's body), or otherwise analyzes the image to identify individuals. The image processing module may include capability or communicate with a correlation module to correlate identified images with thermal (e.g., infrared) images. The fusion subsystem may also include a program module 26 configured as a data retrieval module that retrieves data regarding the identified individual from a database or other storage location, which may be stored in the processing device 12 or retrieved from a remote source. The retrieved data may include health history data for the identified individual, data regarding another individual that has a similar health history, and data describing other events that the identified individual or a similar individual has participated in.

A heat profiling subsystem may include a program module 26 configured as a temperature monitoring module that receives IR images, identification information and health history data (if available), and calculates a heat profile of the identified participant. The temperature monitoring module determines whether any individual is exhibiting body temperatures that exceed a threshold, exhibits high rates of temperature increase, or are otherwise inconsistent with an individual's history. The temperature monitoring module may determine based on the heat profile whether a health risk to the participant exists.

A notification analytics subsystem may include a program module 26 configured as a notification module that receives identification information, temperature information and/or health information and determines an appropriate action to be taken in response to a health risk being present. Examples of actions include generating an alert, alarm or other indication to a user of the computing device 12, transmitting an alert to an official or other authority, and transmitting an alert to an individual participant (e.g., via the participant's mobile phone or wearable device).

The components shown in FIG. 1 and described herein are provided for illustrative purposes and are not intended to be limiting. It should be understood that although not shown, other hardware and/or software components could be used in conjunction with the processing device 12. Examples, include, but are not limited to: microcode, device drivers, redundant processing units, external disk drive arrays, RAID systems, tape drives, and data archival storage systems, etc.

The processing device 12 may be described in the general context of computer system executable instructions, such as program modules, being executed by a computer system. Generally, program modules may include routines, programs, objects, components, logic, data structures, and so on that perform particular tasks or implement particular abstract data types. The processing device 12 may be practiced in distributed cloud computing environments where tasks are performed by remote processing devices that are linked through a communications network. In a distributed cloud computing environment (an example of which will be described in more detail with reference to FIG. 2), program modules may be located in both local and remote computer system storage media including memory storage devices.

In one or more embodiments, the system 11 and/or components thereof are configured as part of a cloud computing environment. For example, the processing device 12 is a server, client computer or other device or system is part of a cloud computing node. The system 11 and the processing device 12 are only one example of a suitable cloud computing node and is not intended to suggest any limitation as to the scope of use or functionality of embodiments of the invention described herein. Regardless, the cloud computing node is capable of being implemented and/or performing any of the functionality set forth hereinabove.

As part of a cloud computing node, the processing device 12 is operational with numerous other general purpose or special purpose computing system environments or configurations. Examples of well-known computing systems, environments, and/or configurations that may be suitable for use with the processing device 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 2:
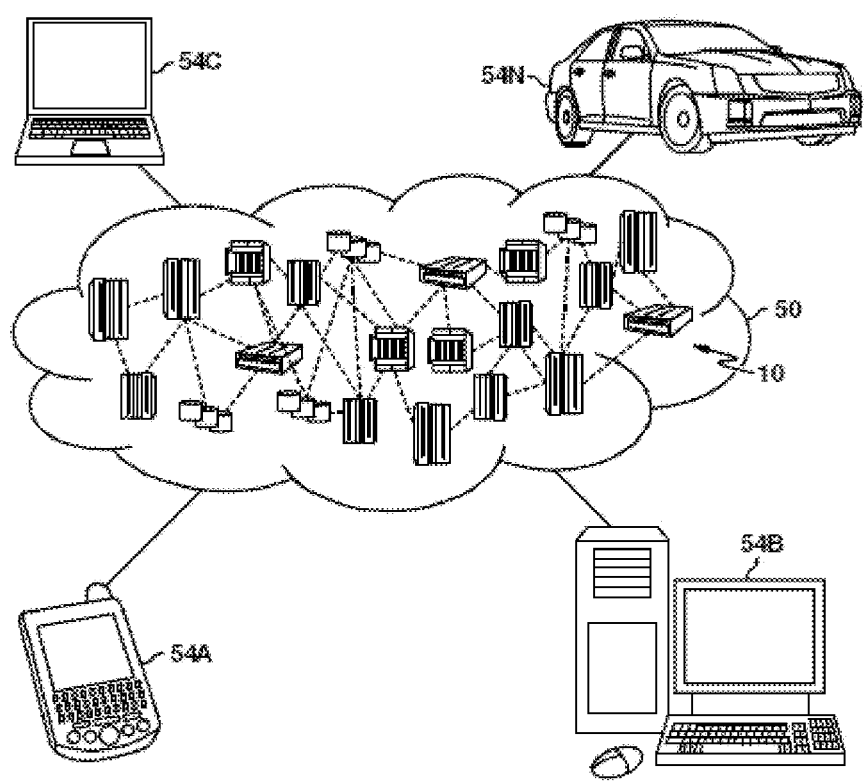
FIG. 2 depicts a cloud computing environment according to an embodiment of the present invention.

Referring now to FIG. 2, an illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. An example of a computing node 10 includes the computing system 11 and/or the processing device 12 discussed above in conjunction with FIG. 1.

Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
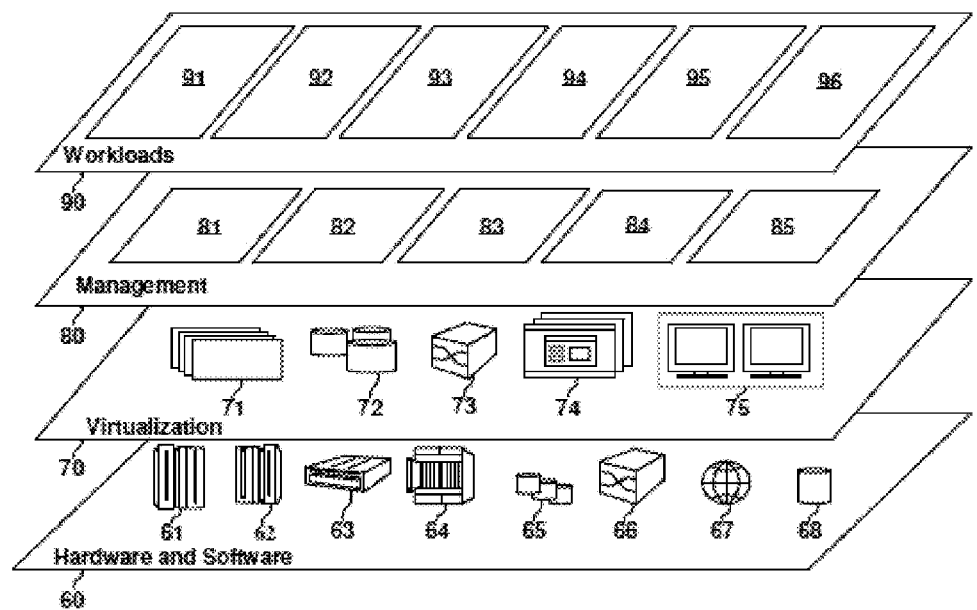
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities (e.g., virtual machines) may be provided: virtual servers 71; virtual storage 72; virtual networks 73, including virtual private networks; virtual applications and operating systems 74; virtual clients 75; and a virtual machine allocation application. In an exemplary embodiment, an application, such as a virtual machine allocation application in the virtualization layer 70, may implement processes or methods for determining and/or performing virtual machine plan generation and allocations as described herein; however, it will be understood that the application may be implemented in any layer.

In another example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and monitoring functions 96 for monitoring of health parameters of individuals in a group in accordance with one or more embodiments of the present invention.

Turning now to an overview of one or more embodiments of the present invention, a processing system or device, such as the processing device 12 (shown in FIG. 1), all or parts of the workload layer 90 (e.g., monitoring functions 96 shown in FIG. 3) and/or one or more processing modules 26 (shown in FIG. 1), is configured to perform health monitoring or tracking of individuals within a group in accordance with one or more embodiments of the present invention. The processing device is in communication (wired or wireless) with one or more IR cameras configured to take IR images or record video of a group of persons, determine a temperature value or profile of each individual (or a subset of the group), and identify each individual and associate the each temperature value or profile with a corresponding individual. The temperature value or profile is compared to a threshold or reference value or profile to determine whether a health risk exists (e.g., excessive body temperature, heat stroke, risk of heat stroke, etc.). The threshold or reference profile may be calculated based on various factors, such as environmental conditions (e.g., amount of sun, ambient temperature, humidity, etc.), and in one or more embodiments is also calculated based on health data associated with the individual. Exemplary health data includes the age of the individual, height and weight, medical records, temperature data from past events, temperature data from similar individuals and/or events, and/or temperature profiles at the start of the event or at previous times during the event.

The threshold or reference profile may be based on (in addition to or in place of data specific to the individual) health history data for another individual or individuals that have similar health history or histories. For example, the reference profile is at least partially based on data regarding another individual that has similar health characteristics (e.g., gender, age, height, weight, medical conditions, performance in a current group event or a similar group event, etc.).

The processing device or system may be configured to monitor multiple participants in parallel. For example, the processing device receives IR images of multiple participants (in a single image or multiple images) and simultaneously determines whether each individual represents a health risk. In addition, the processing device may be configured to perform the monitoring in real time during an event, and perform health monitoring continuously or periodically. Continuous monitoring, in one or more embodiments, refers to the processing device continuously looking for input data from the IR cameras and other devices, and performing health monitoring in real time upon receiving each IR image or set of images.

Figure 4:
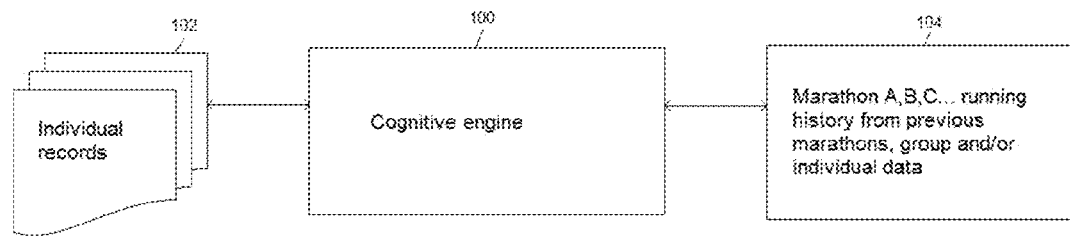
FIG. 4 depicts a computing environment that includes a cognitive engine for monitoring participants in a group event according to an embodiment of the present invention.

FIG. 4 depicts a computing environment that includes a cognitive engine for monitoring participants in a group event according to an embodiment of the present invention. In one or more embodiments, a processing module 26 (shown in FIG. 1) or other processing device includes a cognitive engine 100 that receives identification data in the form of, e.g., individual records 102. The individual records include, for example, names, images, identification numbers, registration information and other identifiers. The cognitive engine 100 also receives health history data in the form of, e.g., records 104 indicating an individual's previous participation in similar events, the individual's performance in such similar events, previous medical history and/or temperature profile data from previous events and/or previous times from the same event. The health history data may include historical data from other individuals who have participated in similar events and/or that have a similar health history. This allows a reference profile including, e.g., an estimate of an acceptable health baseline and an estimate of acceptable rate of temperature change to be known by the system, even if the current group event is the first race or event that the individual has participated in. The cognitive engine 100, in one or more embodiments, performs health monitoring functions in parallel, and can be scaled to massive numbers of participants as a massively-parallel system.

Figure 5:
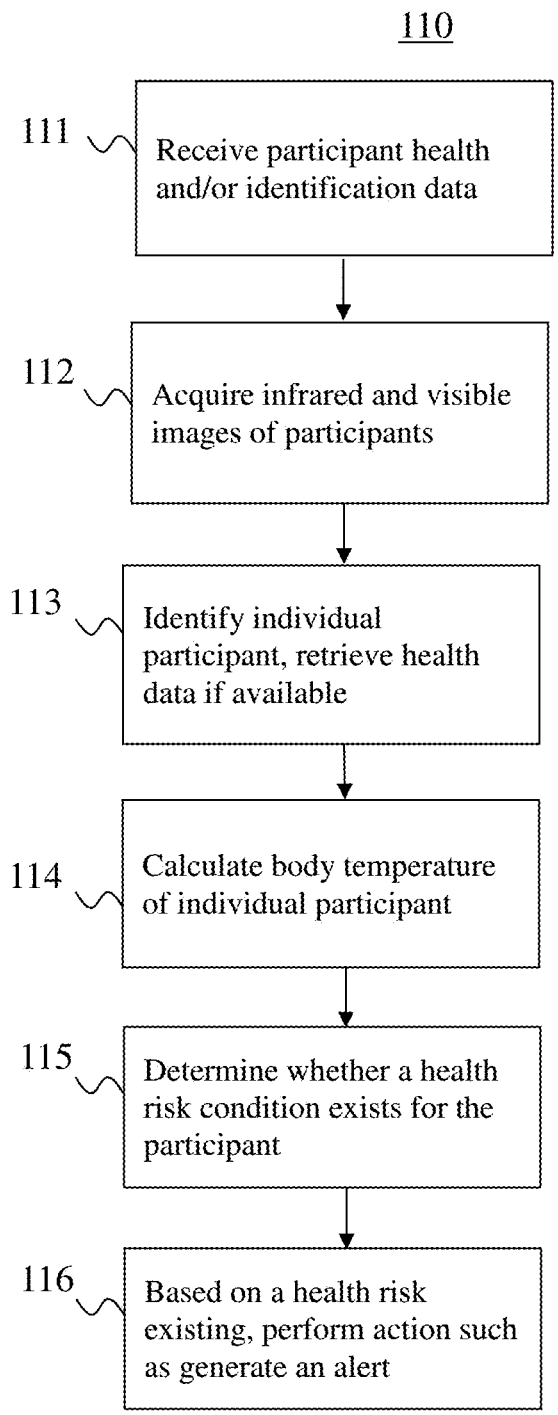
FIG. 5 is a flow diagram depicting a method of monitoring health parameters of individuals in a group according to an embodiment of the present invention.

FIG. 5 is a flow diagram depicting an embodiment of a method 110 of monitoring health parameters of individuals in a group according to an embodiment of the present invention. The method 110 includes a number of steps represented by blocks 111-116. One or more embodiments are described in conjunction with the processing device 12 and/or processing modules 26, but the invention is not so limited. One or more embodiments include the execution of all of the steps shown in blocks 111-116 in the order described. However, certain steps may be omitted, steps may be added, or the order of the steps changed.

The method 110 is discussed in conjunction with an example of a gathering or group of people (also referred to as participants or individuals). In this example, the group of people are participants in a running race, such as a marathon, ten kilometer (10K) or five kilometer (5K) race. It is understood that this example is discussed for illustrative purposes and is not intended to limit the applicability of the method 110. The method 110 may be performed in conjunction with any kind of event or gathering where health or temperature monitoring of individuals within a group is desired. Other examples include sporting events (where monitoring may be performed in relation to the athletes and/or the spectators), concerts, fairs, practices, school events, sport and fitness classes, gym classes, and others.

In step 111, the processing device receives identification data and available health history data for each participant or competitor. Examples of identification data for a participant include an image or images of the participant, name, and an identifier such as a number assigned to the participant. For example, each participant in a race may be given a different number that is displayed on the body. Identification data may also include identifiers or signals for devices worn on the participant's body, such as a tracking chip, wearable device and/or smartphone.

Health history data includes any data that can be used by the processing device to evaluate temperature information acquired during the event and determine whether a health risk exists. Examples of health history data include medical records and information regarding previous race or events. For example, if a participant has participated in past races, available temperature data for the participant may be evaluated. Health history data may also include temperature data collected during the current event or race. The health history data may include data specific to the participant and/or data specific to one or more other participants that have similar health histories and/or characteristics.

Health history data may also include more generalized data. For example, data may be collected for previous races, such as the length, terrain and weather associated with previous races. Temperature data collected from previous races may be used to determine acceptable temperature levels for typical participants, which can be used to calculate temperature values and rate of change considered acceptable. For example, information regarding the current race (e.g., length, weather conditions) may be compared to history data for previous races, and previous races having similar attributes may be used to calculate acceptable temperature characteristics.

In one or more embodiments, the health history data and generalized data is analyzed to calculate or estimate an acceptable temperature profile for a participant, which is also referred to as a reference profile. The reference profile may include an acceptable temperature range and/or acceptable rates of temperature change or increase. In addition, the profile may account for different phases of the event. For example, the temperature range of the participant may be lower during early phases of a race than at later phases of the race. The reference profile may be used during the event to monitor the participant and determine whether the participant is too hot (or cold if an event is in a cold environment where, e.g., hypothermia could be an issue) and/or whether the participant's temperature is increasing (or decreasing) too rapidly.

In step 112, thermal images are collected (e.g., by a monitoring subsystem) during the event from thermal image capturing devices such as IR cameras disposed at various locations. For example, if the event is a race, IR cameras may be positioned at checkpoints and at the finish line. One or more IR cameras may be mounted on a drone or wires to allow the IR camera to follow participants as desired.

In one or more embodiments, visible images of the event are collected from visible light cameras. The visible light cameras may be located at fixed points (e.g., checkpoints) on drone or wires, and/or operated by persons such as race or event photographers, spectators, reporters and event crew.

Additional information may be collected from individual participants. For example, physiological information such as temperature, heart rate, respiration and others may be collected from smartwatches or other monitoring devices worn by participants.

In step 113, data from thermal images (e.g., captured by the IR cameras) is combined with identification data (e.g., by a fusion subsystem) to identify individual participants within a group captured by the IR cameras and retrieve associated health history data.

Figure 6:
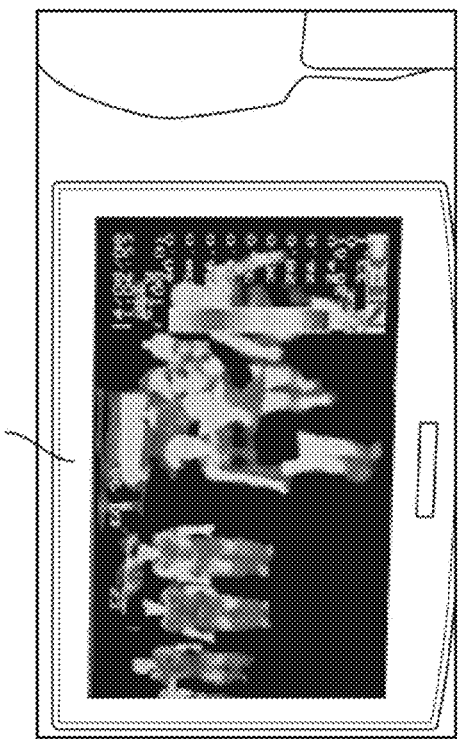
FIG. 6 depicts an example of an infrared image and a visible light image that can be used to perform a method according to an embodiment of the present invention.
Figure 6:
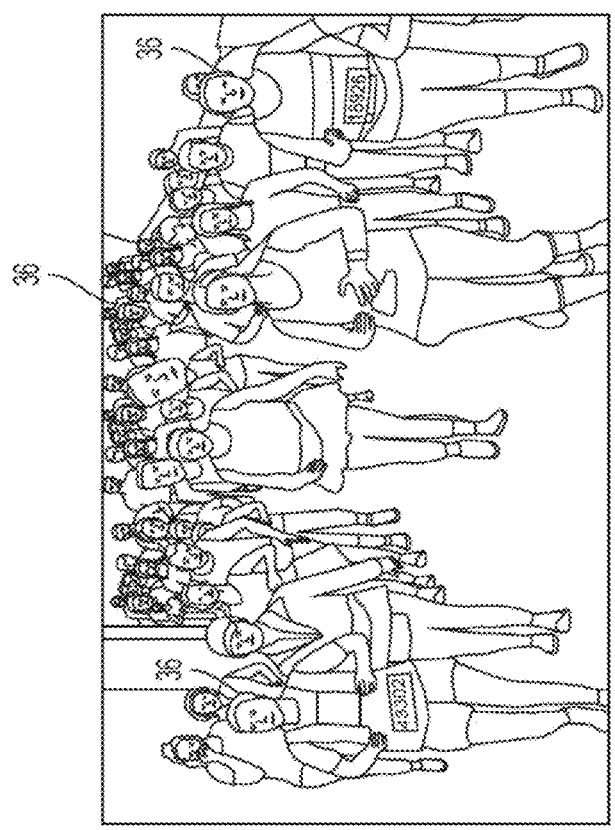

In one or more embodiments, the identification data includes information gathered from visible camera images. In one or more embodiments, individuals depicted by an IR image are correlated with individuals depicted by a visible image taken from a digital camera at the same or a similar location. FIG. 6 depicts an example of an infrared image and a visible light image that can be used to perform the method 110 according to an embodiment of the present invention. In the example of FIG. 6, an IR image taken by an IR camera 38 is shown in combination with a visible image of participants 36. The visible image and the IR image may be fused to correlate individuals. Individuals are identified by, e.g., facial recognition or by identifying a number tag or other visual indicator on individuals. For each individual that is identified, associated health history data is retrieved.

Individuals can be identified using other data in addition to or in place of the visible images. For example, if a participant is wearing a GPS device or tracking chip, the time and location at which the image was taken can be correlated with the positions of individual participants based on the individual's location. In another example, individuals are identified based on visible images, embedded race tracking chips, and/or portable electronic devices tied to participants' identities (e.g., smartwatches, smartphones, etc.)

In step 114, a body temperature profile is calculated for each identified participant (e.g., by a heat profiling subsystem). The body temperature profile may be one or more temperature values, temperature values for different areas of the participant, and/or a temperature curve or other data set depicting changes in temperature over time.

The temperature profile may be combined with other physiological information for use in evaluating the health of the participant. For example, other physiological characteristics are collected where available, such as blood pressure, blood oxygen level, body temp, respiration, etc.

In step 115, each identified participant is evaluated to determine whether any health risks or adverse health effects are present or imminent. In one or more embodiments, the temperature profile is compared to the reference profile. If the temperature profile is outside an acceptable value or range, the processing device or component thereof (e.g., the heat profiling subsystem) determines that a health risk exists. A health risk may exist, for example, the participant's heat profile exceeds a threshold value, is outside an acceptable range, or increases at a rate that exceeds a threshold rate.

In addition to, or in place of, comparing the temperature profile to the reference profile, the processing system may evaluate the participant based on other health or physiological information. For example, facial recognition and/or body analysis algorithms may be used to determine whether the participant's facial gestures or body gestures indicates excessive fatigue or body temperature. Additional biosensor input (e.g., blood pressure, blood oxygen level, body temp respiration, etc.) may be analyzed if available.

Health evaluation may be performed by comparing temperature and/or physiological information with information collected at previous times. For example, images from previous times can be compared to current images to judge degradation of running form over time during the race.

Evaluation of a participant may include generating predictive estimates for generating reference profiles for future times. For example, if a participant's surface temperature is increasing steadily without regulation, the surface temperature can be projected to a future time or for a future checkpoint, and the projected temperature can be used to estimate a reference profile temperature for the future time or checkpoint.

In step 116, the processing device performs one or more actions based at least in part or at least partially in response to determining that a health risk is present for a participant. In one or more embodiments, the processing device display or transmits an alert, warning or other indication that a health risk is present.

For example, the processing device can send a notification to a participant on their smartwatch or mobile devise, to officials and/or health professionals. The notification may include real-time recommendations of optimal medical staff allocation, e.g., recommendations that inform race officials as to who and where to help, and services that should be provided. In one example, the notification and accompanying health information may be transmitted to the participant and to an electronic board as part of the race logistics.

The processing device may transmit information to the participant, an official and/or other user. For example, the processing device may include a display or transmit data to a display on another device (e.g., a participant's smartphone) that provides information related to the health monitoring. The information may include, for example, cognitive analysis of health information, GPS course information, temperature as a function of IR camera output, running form, etc. The information may also include guidance to the participant to remediate potential health risks. For example, the processing device can provide suggestions to the participant regarding increase or decrease the participant's speed.

Figure 7:
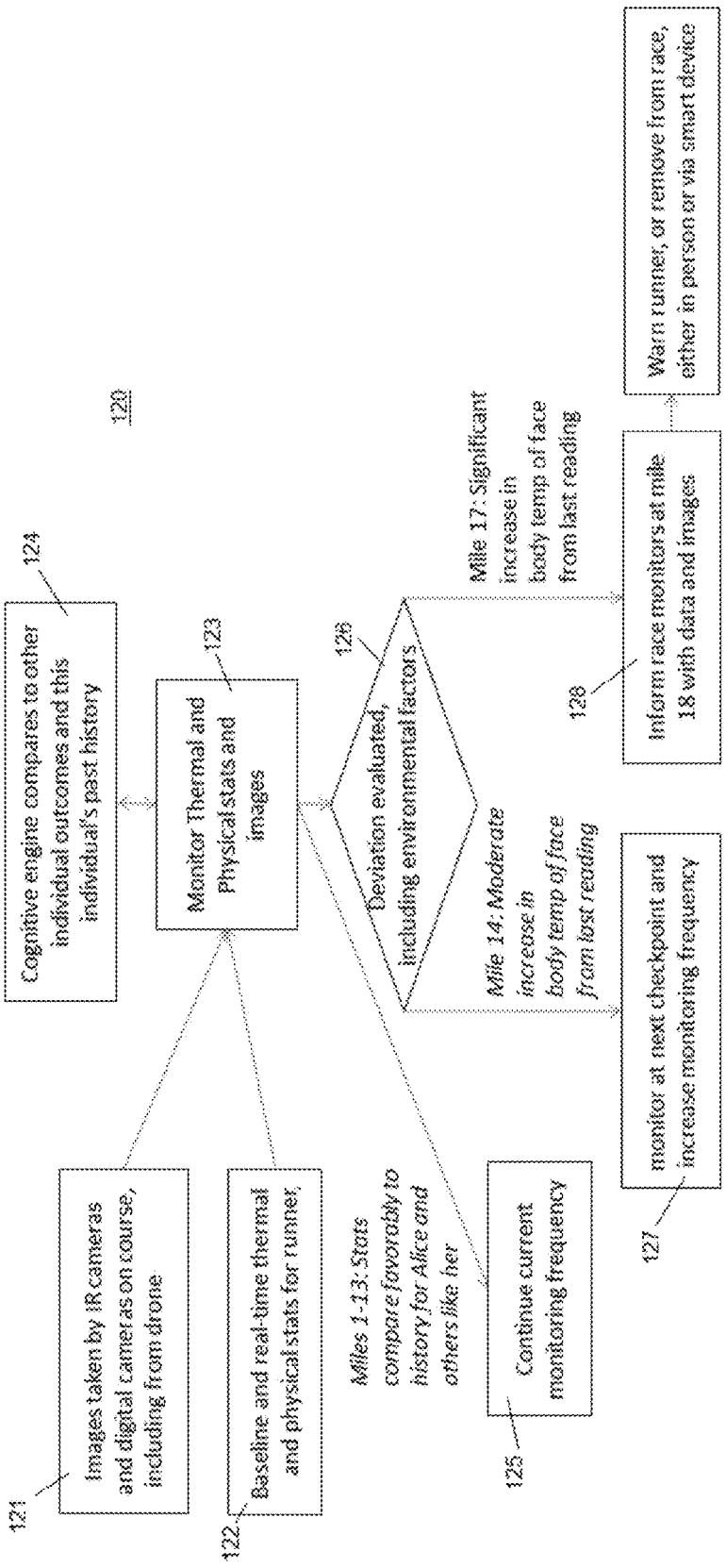
FIG. 7 is a flow diagram depicting an example of a method according to an embodiment of the present invention for monitoring health parameters of individual athletes participating in an athletic event.

FIG. 7 is a flow diagram depicting an example of a method 120 according to an embodiment of the present invention for monitoring health parameters of individual athletes participating in an athletic event. Steps of the method 120 in this example are represented in FIG. 7 as blocks 121-128. In this example, the method 120 is performed for each of a plurality of athletes participating in a road race (e.g., a marathon). It is to be understood that the method steps performed in this example may be performed in parallel for any number of athletes. It is also to be understood that this example may be applicable to any type of gathering or event for which temperature and health monitoring is desired.

During the race, images from an IR camera are continuously collected for each participant at each location (e.g., at a first race checkpoint) of an IR camera or cameras (block 121). For example, the body temperature of each runner is monitored by IR cameras at the start, finish, and periodic milestone gates coupled with visual cameras.

In one or more embodiments, IR and/or visible cameras are located on a drone that follows an individual runner or group of runners. Baseline temperature statistics (e.g., a reference profile) and available real time temperature and/or other physiological statistics (biosensor input from smartwatch/wearable) is collected (block 122).

Image data and statistics are input to a monitoring model (block 123) that calculates a temperature profile, and a cognitive engine or other suitable processing device or module evaluates the temperature profile as discussed above to determine whether a health risk is present (block 124). In this example, the evaluation is performed periodically at a selected frequency and deviations from a reference value or range are calculated (block 125). If no deviations are detected, the evaluation is performed at the current location and a subsequent location (e.g., a second checkpoint) at the same frequency.

If a deviation is detected, the magnitude of the deviation is evaluated (block 126), and the monitoring module can take various actions depending on the magnitude of the deviation. For example, if the deviation is less than or equal to a selected magnitude (e.g., a moderate deviation), the monitoring frequency is increased for the subsequent location (block 127). If the deviation is greater than the selected magnitude, the monitoring module generates an alert or other indication to the runner and/or a race official that there may be a health risk (block 128). The alert can be, e.g., posted on an electronic board as part of the race logistics, shared with race officials or crew and/or shared with the runner's wearable if available. The alert may include recommendations for reducing the risk. If the deviation is high enough, the alert may recommend that the runner be removed from the race.

Embodiments described herein can be applied to any of various events and situations. For example, in an indoor location such as a school gym, IR cameras provide a live feed of IR images to the processing device. The processing device evaluates individuals in the indoor location, identify individuals exhibiting indications of a health risk (e.g., danger of overheating), and notify such individuals or another person (e.g., a teacher) and recommend appropriate response, such as recommending a break and fluid intake. In addition to notifications, the processing device can take other actions to address health risks. For example, the cognitive engine records the skin temperature of individuals and adjusts the room temperature (energy consumption) based on a map of where people are and what their body temperature is.

Technical effects and benefits include the ability to effectively monitor athletes or participants in a sporting event or other gathering and prevent adverse health effects without interfering with individuals or the event. Embodiments described herein allow for the detection of risks, such as the risk of heatstroke or hypothermia, which may go unnoticed by the athlete during their competition, but can have adverse effects to health and performance if not addressed, e.g., by cooling off or warming up as appropriate.

In events such as races or other sporting events, participants may not have wearable temperature sensors, due to preference or limitations on wearables for that sport. In addition, large numbers of participants make individualized health tracking and health event prediction difficult for race organizers and medical staff. Embodiments described herein address such challenges and enhances health and performance outcomes for participants.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A system for monitoring participants in a group, the system comprising:
   one or more thermal image capturing devices disposed at a location configured to capture one or more thermal images of a plurality of participants in an event;
   one or more visible image capturing devices configured to capture one or more visible light images of the plurality of participants, and
   a processing device communicably coupled to the one or more thermal image capturing devices, the once or more visible image capturing devices and an identification database, the processing device configured to receive a thermal image of the plurality of participants and a visible light image of the plurality of participants during the event, and receive identification data for at least one individual participant of the plurality of participants from the identification database, the processing device configured to perform a method during the event, the method comprising:
   identifying by an image processing module the at least one individual participant of the plurality of participants based on the one or more visible light images;
   correlating the at least one individual participant depicted by the one or more visible light images to the at least one individual participant depicted by the thermal image, wherein the correlating includes fusing the visible light image and the thermal image;
   calculating by a temperature monitoring module a heat profile of the at least one individual participant based on the thermal image;
   comparing, by a temperature monitoring module, the heat profile to a reference profile, the reference profile generated based on the identification data, determining whether a deviation exists between the heat profile and the reference profile, and based on detecting the deviation, calculating a magnitude of the deviation and determining whether a health risk exists based on the magnitude of the deviation; and
   generating a notification based on determining that the health risk exists.

2. The system of claim 1, wherein event is an athletic event.

3. The system of claim 1, wherein the one or more thermal image capturing devices include one or more infrared cameras, and the one or more thermal images include one or more infrared images.

4. The system of claim 1, wherein the monitoring module collects the thermal images from thermal image capturing devices disposed at multiple locations to capture successive images of the at least one individual participant over time, and calculating the heat profile and comparing are performed periodically at a selected frequency at each of the multiple locations.

5. The system of claim 4, wherein the processing device is further configured to perform:
   based on the deviation being less than or equal to a selected value, generating the notification and performing the comparing at a subsequent location at a higher frequency than the selected frequency; and
   based on the deviation being greater than the selected value, generating a notification that recommends actions to be taken to ameliorate the health risk.

6. The system of claim 1, wherein the processing device is configured to perform the method for each of the at least one individual participant of the plurality of participants in parallel.

7. The system of claim 1, wherein the identification data includes an image and associated identification information for each participant, and identifying the at least one of the plurality of participants is performed in conjunction with the one or more visible light images based on facial recognition.

8. The system of claim 1, wherein the reference profile of a participant is based on historical data from at least one of: one or more previous events attended by the participant, one or more previous events attended by another person and data regarding a health history of another person.

9. The system of claim 1, wherein the notification indicates that the health risk is present and provides one or more recommendations for ameliorating the health risk.

10. A computer implemented method of monitoring participants in a group, the method comprising:
    receiving identification data for at least one of a plurality of participants in an event from an identification database;
    collecting one or more thermal images of the plurality of participants by a monitoring module during the event;
    collecting one or more visible light images of the plurality of participants by one or more visible image capturing devices during the event,
    receiving, by an image processing module, a thermal image of the plurality of participants and a visible image light image of the plurality of participants during the event, receiving the identification data, and identifying the at least one individual participant of the plurality of participants based on the one or more visible light images;

correlating the at least one individual participant depicted by the one or more visible light images to the at least one individual participant depicted by the thermal image, wherein the correlating includes fusing the visible light image and the thermal image;

calculating a heat profile of the at least one individual participant by a temperature monitoring module based on the thermal image;

comparing, by the temperature monitoring module, the heat profile to a reference profile, the reference profile generated based on the identification data, determining whether a deviation exists between the heat profile and the reference profile, and based on detecting the deviation, calculating a magnitude of the deviation and determining whether a health risk exists based on the magnitude of the deviation; and generating a notification based on determining that the health risk exists.

11. The method of claim 10, further comprising transmitting the notification to the at least one of: the least one individual participant, an official and a health professional.

12. The method of claim 10, wherein the monitoring module collects the thermal images from thermal image capturing devices disposed at multiple locations to capture successive images of the at least one individual participant over time, and calculating the heat profile and comparing are performed periodically at a selected frequency at each of the multiple locations.

13. The method of claim 12, further comprising:

based on the deviation being less than or equal to a selected value, generating the notification and performing the comparing at a subsequent location at a higher frequency than the selected frequency; and based on the deviation being greater than the selected value, generating a notification that recommends actions to be taken to ameliorate the health risk.

14. The method of claim 10, wherein the method is performed for each of the at least one individual participant of the plurality of participants in parallel.

15. The method of claim 10, wherein the identification data includes an image and associated identification information for each participant, and identifying the at least one individual participant of the plurality of participants is performed in conjunction with the one or more visible light images based on facial recognition.

16. The method of claim 10, wherein the reference profile for a participant is based on historical data from one or more previous group events attended by the participant.

17. A computer program product for monitoring participants in a group, the computer program product comprising a non-transitory computer readable storage medium having program instructions embodied therewith, the program instructions executable by a processor to cause the processor to perform:

receiving identification data for at least one of a plurality of participants in an event from an identification database;

collecting one or more thermal images of the plurality of participants by a monitoring module during the event;

collecting one or more visible light images of the plurality of participants by one or more visible image capturing devices during the event;

receiving, by an image processing module, a thermal image of the plurality of participants and a visible image light image of the plurality of participants during the event, receiving the identification data, and identifying the at least one of the plurality of participants based on the one or more visible light images;

correlating the at least one individual participant depicted by the one or more visible light images to the at least one individual participant depicted by the thermal image, wherein the correlating includes fusing the visible light image and the thermal image;

calculating a heat profile of the at least one individual participant by a temperature monitoring module based on the thermal image;

comparing the heat profile to a reference profile, the reference profile generated based on the identification data, determining whether a deviation exists between the heat profile and the reference profile, and based on detecting the deviation, calculating a magnitude of the deviation and determining whether a health risk exists based on the magnitude of the deviation; and generating a notification based on determining that the health risk exists.

18. The computer program product of claim 17, wherein the program instructions cause the processor to perform transmitting the notification to the at least one of: the least one individual participant, an official and a health professional.

19. The computer program product of claim 17, wherein the monitoring module collects the thermal images from thermal image capturing devices disposed at multiple locations to capture successive images of participants over time.

20. The computer program product of claim 19, wherein calculating the heat profile and comparing are performed periodically at a selected frequency at each of the multiple locations, and the method further comprises:

based on the deviation being less than or equal to a selected value, generating the notification and performing the comparing at a subsequent location at a higher frequency than the selected frequency; and based on the deviation being greater than the selected value, generating a notification that recommends actions to be taken to ameliorate the health risk.

* * * * *